Figure 1:
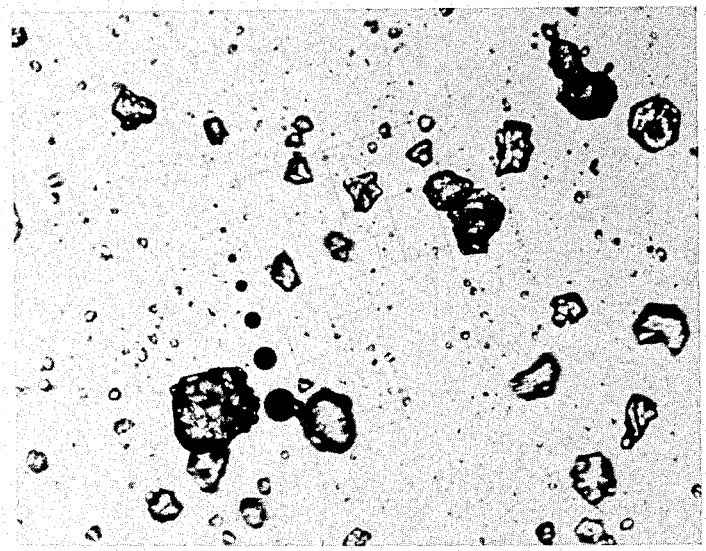

United States Patent [19]

Brodie

[11] Patent Number: 4,493,933
[45] Date of Patent: Jan. 15, 1985

[54] MANUFACTURE OF ANTIBIOTICS

[75] Inventor: Alastair C. Brodie, Ickenham, England

[73] Assignee: Glaxo Group Limited, London, England

[21] Appl. No.: 441,247

[22] Filed: Nov. 12, 1982

[30] Foreign Application Priority Data

Nov. 13, 1981 [GB] United Kingdom ............... 8134358

[51] Int. Cl.³ ........................................... C07D 277/40
[52] U.S. Cl. ....................................... 548/194; 544/25
[58] Field of Search ....................................... 548/194

[56] References Cited

U.S. PATENT DOCUMENTS

| 4,166,115 | 8/1979 | Takaya et al. | 424/246 |
| 4,258,041 | 3/1981 | O'Callaghan et al. | 424/246 |
| 4,288,434 | 9/1981 | Heymes | 424/246 |
| 4,294,960 | 10/1981 | Takaya et al. | 544/22 |

Primary Examiner—Robert Gerstl
Attorney, Agent, or Firm—Bacon & Thomas

[57] ABSTRACT

The invention provides crystalline (Z)-2-(2-t-butoxycarbonyl-prop-2-oxyimino)-2-(2-triphenylmethylaminothiazol-4-yl)acetic acid in association with dioxan and its crystalline ethyl ester in association with methanol. The compounds are of value as intermediates in the preparation of $\beta$-lactam antibiotics such as ceftazidime or azthreonam.

5 Claims, 2 Drawing Figures

MANUFACTURE OF ANTIBIOTICS

This invention relates to improvements in or relating to the manufacture of antibiotics. More particularly it relates to new compounds that are of value in the synthesis of certain β-lactam antibiotics, for example cephalosporins and 2-oxoazetidines.

A number of antibiotics compounds are now known which have a 2-(2-aminothiazol)-4-yl)-2-(substituted oxyimino)acetamido side-chain e.g. in the 7-position of cephalosporins. One such antibiotic, (6R,7R)-7-[(Z)-2-(2-aminothiazol-4-yl)-2-(2-carboxyprop-2-oxyimino)-acetamido]-3-(1-pyridiniummethyl)ceph-3-em-4-carboxylate, hereinafter called "ceftazidime" is described, inter alia, in our U.S. Pat. No. 4,258,041 and details of its preparation are given therein.

One general method for preparing ceftazidime involves building up the 7-position side chain through a series of reactions to form the side-chain acid or a reactive derivative thereof followed by coupling with the 7β-amino cephalosporin nucleus. A series of such reactions for the preparation of a protected form of the 7-side chain is described in Preparations 1 to 4 of the above-mentioned U.S. patent specification. Two of the intermediates described in these preparations are (Z)-2-(2-t-butoxycarbonylprop-2-oxyimino)-2-(2-triphenylmethylamino-thiazol-4yl)acetic acid and its ethyl ester.

We have now found that it is possible to prepare improved forms of these intermediates that are of value in the preparation of β-lactam antibiotics e.g. ceftazidime.

Viewed from one aspect, therefore, we provide crystalline (Z)-2-(2-t-butoxycarbonylprop-2-oxyimino)-2-(2-triphenylmethylaminothiazol-4-yl)acetic acid in association with 0.1 to 0.6 moles of dioxan per mole of acid, and its crystalline ethyl ester in association with 0.4–2 moles of methanol per mole of ester.

We have found the new dioxan associated acid to be of improved quality and of provide a number of advantages on a manufacturing scale. We have found (Z)-2-(2-triphenylmethylaminothiazol-4-yl)acetic acid as previously prepared on a manufacturing scale to possess a number of disadvantages in particular poor handling characteristics. Thus this material has a variable form which changes on mechanical handling. It is therefore difficult to transfer it from its isolation vessel to a filter and satisfactory mechanical filtration is impossible. In contrast, the dioxan-associated acid precipitates much more easily, has a consistent, well-defined crystalline structure and can readily be filtered, washed and dried. Overall, the dioxan-associated compound of the invention is of considerable advantage in manufacturing terms.

The acid is preferably associated with from 0.1–0.4 moles of dioxan per mole of (Z)-2-(2-t-butoxycarbonylprop-2-oxyimino)-2-(2-triphenylmethylamino-thiazol-4-yl)acetic acid.

We have found the crystals of the new dioxan-associated acid to have a well defined shape e.g. as shown in FIG. 1 of the accompanying drawings, which shows the crystals at 185×magnification and generally the compound is a free flowing particulate material.

The dioxan-associated acid of the invention may be coupled by methods known in the art with the appropriate antibiotic nucleus, e.g. a 7β-amino cephalosporin, followed by removal of protecting groups that are present, to form the desired antiobiotic.

Examples of β-lactam antibiotics having a (Z)-2-(2-aminothiazol)-4-yl)-2-(2-carboxyprop-2-oxyimino)-acetamido side chain which may be advantageously prepared using the dioxan-associated acid of the invention include ceftazidime and the cephalosporin antibiotics described in our U.K. Patent Specification Nos. 2,029,824A, 2,024,808A, 2,027,691A, 2,040,921A, 2,036,724A, 2,037,281A and 2,046,261A, as well as the monocyclic β-lactam compound azthreonam described in U.K. Patent Specification No. 2,071,650A.

According to another aspect of the invention, we provide a process for the preparation of the dioxanassociated acid of the invention which comprises precipitating the desired product from a solution comprising (Z)-2-(2-t-butoxycarbonylprop-2-oxyimino)-2-(2-triphenylmethylaminothiazol-4-yl)acetic acid and dioxan.

The precipitation may preferably be effected at around room temperature e.g. from 0° to 30° C. The (Z)-2-(2-t-butoxycarbonylprop-2-oxyimino)-2-(2-triphenylmethylaminothiazol-4-yl) acetic acid may if desired be in a solution such as of methanol or aqueous methanol prior to contacting with dioxan. The amount of dioxan with which the solution will generally be contacted may vary within wide limits but an amount of dioxan of from 5 to 25% e.g. of the order of about 10% of the volume of the solution is suitable. A small amount of water may also be added if desired. Alternatively the compound may be precipitated from aqueous dioxan e.g. where the solution contains from 30 to 55% by volume of water.

Prior to the precipitation of the desired compound, the (Z)-2-(2-t-butoxycarbonylprop-2-oxyimino)-2-(2-triphenylmethylaminothiazol-4-yl)acetic acid may be prepared by a variety of synthetic routes. One such route is described in U.S. Pat. No. 4,258,041. A preferred embodiment of this route is the selective hydrolysis of ethyl (Z)-2-(2-t-butoxycarbonylprop-2-oxyimino)-2-(2-triphenylmethylaminothiazol-4-yl)acetate which may first be dissolved in a solvent such as methanol in the presence of a base, such as an alkali metal carbonate, e.g. potassium carbonate. Such a hydrolysis may be conveniently carried out at elevated temperatures e.g. under reflux. The dioxan may then be added directly to the reaction mixture, followed by cooling and acidification to convert the salt, e.g. potassium salt of (Z)-2-(2-t-butoxycarbonylprop-2-oxyimino)-2-(2-triphenylmethylaminothiazol-4-yl)acetic acid formed in the reaction to the free acid. The dioxan-associated acid then precipitates. The precipitated product may, if desired, be recrystallised from dioxan or aqueous dioxan.

Direct advantages of the use of this latter process include a more ready recovery of the methanol used than has been possible hitherto and a decrease in the overall usage of the methanol.

A particularly preferred starting material in this process is the crystalline methanol-associated ethyl (Z)-2(2-t-butoxycarbonylprop-2-oxyimino)-2-(2-triphenylmethylaminothiazol-4-yl) acetate according to the invention. We have found this compound to be of improved quality and to provide a number of advantages on a manufacturing scale. We have found the ethyl (Z)-2-(2-t-butoxycarbonylprop-2-oxyimino)-2-(2-triphenylmethylaminothiazol-4-yl)acetate as previously prepared on a manufacturing scale possesses poor handling characteristics, whereas the new methanol-associated ester can be readily filtered, washed and dried. This its use during the manufacturing process is of considerable advantage.

The ester is preferably associated with from 0.8 to 1.2 moles of methanol per mole of ethyl (Z)-2-(2-t-butoxycarbonylprop-2-oxyimino)-2-(2-triphenylmethylaminothiazol-4-yl)acetate.

Figure 2:
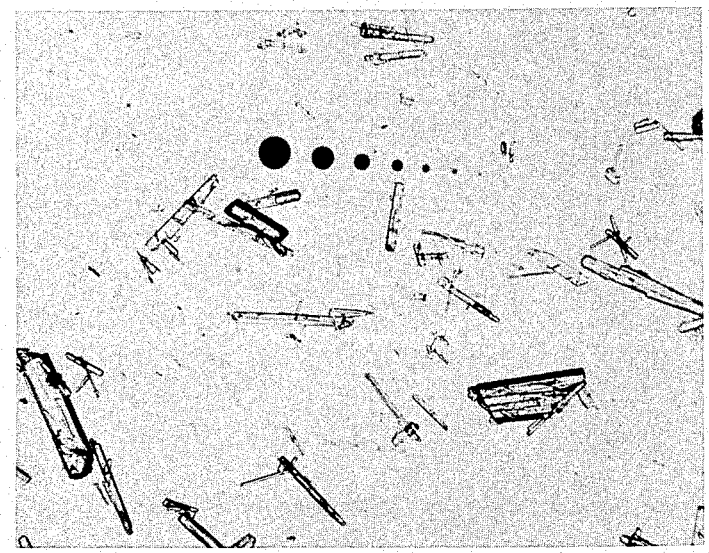

We have found the crystals of the new solvate to have a well defined regular shape e.g. as shown in FIG. 2 of the accompanying drawings, which shows the crystals at 185×magnification and generally the compound is a free-flowing particulate material.

According to yet another aspect of the invention, we provide a process for the preparation of the methanol-associated ester which comprises precipitating the desired product from a solution comprising ethyl (Z)-2-(2-t-butoxycarbonylprop-2-oxyimino)-2-(2-triphenylmethylaminothiazol-4-yl)acetate and methanol.

Prior to precipitation of the desired compound, the ester may be prepared by a variety of synthetic routes. One such route is described in U.S. Pat. No. 4,258,041. The methanol-associated ester may be precipitated directly from methanol. Alternatively, ethyl (Z)-2-(2-t-butoxycarbonylprop-2-oxyimino)-2-(2-triphenylmethylaminothiazol-4-yl)acetate may be dissolved in methanol for example by heating to reflux, the solution cooled and precipitation assisted by addition of for example water, e.g. at a temperature of from 0° to 30° C.

The invention will now be more particularly described in the following non-limiting Examples. All temperatures are in °C.

Dioxan-associated
(Z)-2-(2-t-Butoxycarbonyl-prop-2-oxyimino)-2-(2-triphenylmethylaminothiazol-4-yl)acetic acid

EXAMPLE 1

Methanol-associated ethyl (Z)-2-(2-t-butoxycarbonylprop-2-oxyimino-2-(2-triphenylmethylaminothiazol-4-yl) acetate (31.6 kg) was refluxed for 17 hours in methanol (125 l) to which had been added a solution of potassium carbonate (7.0 kg) in water (12.5 l). At the end of the reflux period the batch was slightly cooled and a mixture of dioxan (15 l) and water (3 l) was added. The batch was then cooled to 15° C. and orthophosphoric acid (16.7 l) was added. The title compound precipitated, was filtered off, washed with water (290 l), and sucked as dry as possible before being recrystallised from a mixture of dioxan (160 l) and water (140 l). The pure material was filtered off, washed with 2:1 dioxan:water (39 l) and acetone (140 l) before being dried in a vacuum oven for 4 hours at 30° C. to give the title compound (25.7 kg).

Water (Karl Fischer): 0.5%
$E_{1cm}^{1\%}$ at 235 nm calculated to dry basis: 387
Solvents by gas chromatography: Dioxan 3.1%, Acetone 0.04%

EXAMPLE 2

Crude (Z)-2-(2-t-butoxycarbonylprop-2-oxyimino)-2-(2-triphenylmethylaminothiazol-4-yl) acetic acid (359.4 g) was dissolved with stirring in dioxan (1.44 l) at about 80° C. Water (720 ml) at 70° was added and the mixture cooled to 15°. The product was collected by filtration and washed with a mixture of dioxan (140 ml) and water (70 ml), then acetone (2×500 ml) and dried in an air oven at 40° to give the title compound (318.5 g).

Water (Karl Fischer): <0.1%
$E_{1cm}^{1\%}$ at 235 nm calculated to dry basis: 388
Solvents by gas chromatography: Dioxan 2.4%, Acetone 0.06%

EXAMPLE 3

Methanol-associated ethyl (Z)-2-(2-t-butoxycarbonylprop-2-oxyimino)-2-(2-triphenylmethylaminothiazol-4-yl)acetate (25.0 kg) was refluxed for 17 hours in methanol (180 l) to which had been added a solution of potassium carbonate (5.95 kg) in water (18.1.). At the end of the reflux period the batch was slightly cooled and a mixture of dioxan (12.1) and water (2.4 l.) was added. The batch was then cooled to 15° C. and orthophosphoric acid (specific gravity 1.5, 11.4 l.) was added. The title compound precipitated, was filtered off, washed with water (386 l. containing 0.8 g polyethylene glycol 600 mono-oleate), and sucked as dry as possible before being recrystallised from a mixture of dioxan (95.1) and water (83.4 l.). The pure material was filtered off, washed with acetone (38 l.) before being dried in a vacuum oven for 3½ hours at 30° C. to give the title compound (19.8 kg)

Water (Karl Fischer): <0.1%
$E_{1cm}^{1\%}$ at 235 nm calculated to dry basis: 415
Solvents by gas chromatography (% w/w): Dioxan 3.5, Acetone <0.1

EXAMPLE 4

Methanol-associated Ethyl (Z)-2-(2-t-butoxycarbonylprop-2-oxyimino)-2-(2-triphenylmethylaminothiazol-4-yl) acetate Ethyl (Z)-2-hydroxyimino-2-(2-triphenylmethylaminothiazol-4-yl) acetate hydrochloride (19.7 kg) stirred in N,N-dimethylformamide (62 l) was treated with t-butyl-2-bromo-2-methylpropionate (10.5 kg) and potassium carbonate (5 kg) at ambient temperature. Further potassium carbonate (3×5 kg) was added at 2, 4 and 6 hours at which time 40° had been attained.

After 22 hours stirring at about 40° the mixture was cooled to 8° and water (270 l) at 2° was added during 15 minutes. The resulting slurry was filtered and the solid washed with cold water (260 l) and sucked dry. The filter cake (37 kg) was heated at reflux in methanol (270 l) until it was dissolved when water (22 l) was introduced and the mixture cooled slowly at a temperature of 5°. The crystallised solid was collected, washed with methanol (55 l) and dried in an air oven at room temperature for 72 hours to give the title compound (22.5 kg). Gas liquid chromatography showed a methanol content of 4.9%.

I claim:

1. Crystalline (Z)-2-(2-t-butoxycarbonylprop-2-oxyimino)-2-(2-triphenylmethylaminothiazol-4-yl)acetic acid in association with 0.1 to 0.6 moles of dioxan per mole of acid.

2. The dioxan-associated acid according to claim 1 wherein each mole of (Z)-2-(2-t-butoxycarbonylprop-2-oxyimino)-2-(2-triphenylmethylaminothiazol-4-yl)acetic acid is associated with 0.1 to 0.4 moles of dioxan.

3. The dioxan-associated acid according to claim 1 in the form of a free-flowing particulate material.

4. A process for the preparation of the dioxan-associated acid according to claim 1 which comprises precipitating the desired product from a solution comprising (Z)-2-(2-t-butoxycarbonylprop-2-oxyimino)-2-(2-triphenyl-methylaminothiazol-4-yl)acetic acid and dioxan.

5. A process according to claim 4 wherein the precipitated compound is recrystallised from dioxan or aqueous dioxan.

* * * * *